United States Patent [19]

Miller et al.

[11] Patent Number: 5,758,650
[45] Date of Patent: Jun. 2, 1998

[54] UNIVERSAL NEEDLE GUIDE FOR ULTRASONIC TRANSDUCERS

[75] Inventors: Swend L. Miller, Kent; Gary D. Ninneman, Issaquah, both of Wash.

[73] Assignee: Siemens Medical Systems, Inc., Iselin, N.J.

[21] Appl. No.: 724,122

[22] Filed: Sep. 30, 1996

[51] Int. Cl.⁶ .................. A61B 8/00; A61B 10/00
[52] U.S. Cl. ..................... 128/662.05; 128/754
[58] Field of Search ............ 606/96, 130; 128/662.05

[56] References Cited

U.S. PATENT DOCUMENTS

| | | |
|---|---|---|
| 4,058,114 | 11/1977 | Soldner . |
| 4,346,717 | 8/1982 | Haerten . |
| 4,489,730 | 12/1984 | Jingu ........................ 128/662.05 |
| 4,571,243 | 2/1986 | Froning et al. ............ 606/130 X |
| 4,635,644 | 1/1987 | Yagata . |
| 4,681,103 | 7/1987 | Boner et al. . |
| 4,742,829 | 5/1988 | Law et al. . |
| 4,883,059 | 11/1989 | Stedman et al. . |
| 4,911,173 | 3/1990 | Terwilliger . |
| 5,052,396 | 10/1991 | Wedel et al. ............. 128/662.05 |
| 5,076,279 | 12/1991 | Arenson et al. . |
| 5,095,910 | 3/1992 | Powers . |

OTHER PUBLICATIONS

1995–1996 product catalog of AMEDIC AB, Sollentuna, Sweden, exact publication date unknown, pp. 6, 18, 19, 28.

Primary Examiner—Francis Jaworski
Attorney, Agent, or Firm—Jeffrey Slusher

[57] ABSTRACT

A guide for guiding a needle for insertion into a patient during a surgical procedure has a main guide body, a mounting arrangement for attaching the main guide body onto an ultrasound probe, and a needle cap that fits removably onto the needle guide. At least one channel is located between the main guide body and the needle cap. The needle cap is preferably made of a magnetic metal, and a magnet is preferably mounted in the main guide body. The needle cap is thus removably held on the main guide body by the force of the magnet. A multi-angle embodiment of the invention has a plurality of channels, each having a different, predetermined guide angle. The mounting arrangement preferably is in the form of a adjustable clamp, with a first and a second arm, which engage the housing of the ultrasound probe. The second arm preferably pivots in the main guide body depending on the position of an adjustment arrangement such as a thumbscrew.

4 Claims, 4 Drawing Sheets

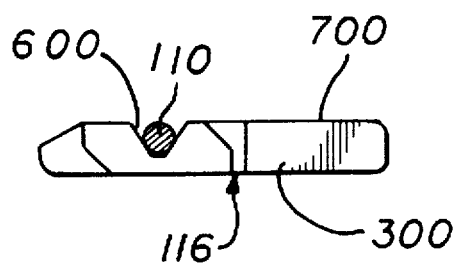
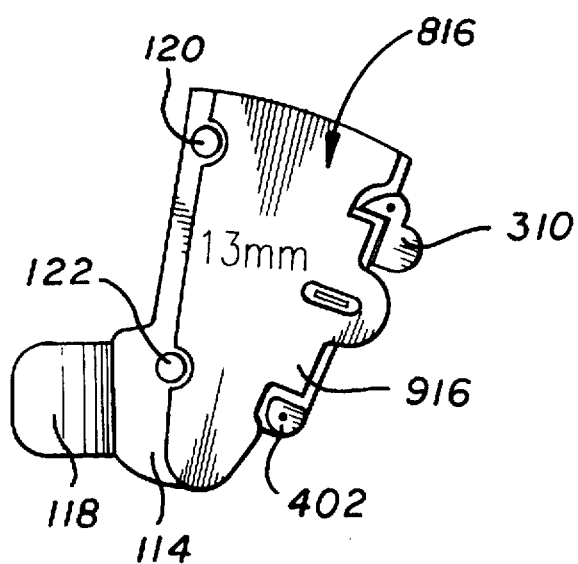
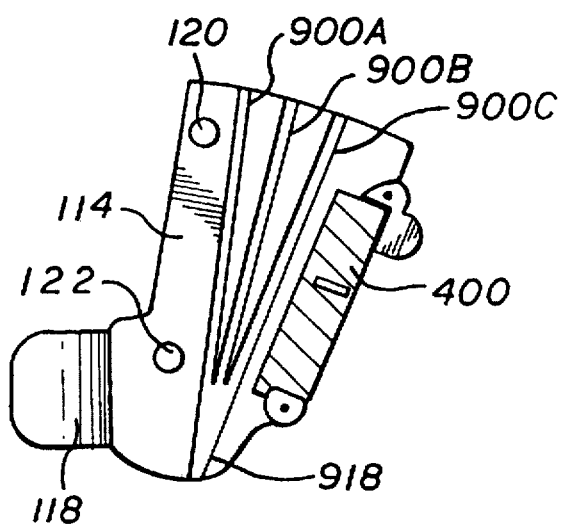

UNIVERSAL NEEDLE GUIDE FOR ULTRASONIC TRANSDUCERS

BACKGROUND OF THE INVENTION

1. Field of the Invention

This invention involves a device that can be attached to an ultrasound probe for guiding a needle, for example, a biopsy needle, into a patient, while an operator follows the needle's course by viewing an ultrasonic image.

2. Description of the Related Art

Many surgical procedures involve inserting a needle or cannula into a patient while viewing an image of the region of insertion. These include such procedures as needle biopsy, drainage, amniocentesis, precision injections, cell aspiration, and radio-frequency cauterization. For example, ultrasonic imaging is often used to guide the insertion of a biopsy needle in order to more accurately obtain a tissue sample from a region of interest. Such image aided needle insertion may also be helpful when one wants to inject or extract a fluid into or from a precisely defined place within the patient.

During these procedures, an ultrasonic probe is held against the patient's body, usually along with some coupling agent. An image of the area of the body adjacent to or near the probe is then created and displayed using conventional ultrasonic imaging techniques while the physician inserts the needle and guides it towards its target. Both the needle's tip and at least a portion of the target are visible on the display.

When inserting a needle into a patient, failure to heed the well-known maxim "navigare necesse est" ("navigation is necessary") may lead not only to an inaccurate tissue sample, but may also require the physician to reinsert the needle. The disadvantages of such an error will be obvious to even the most stoic who imagine themselves the hapless, cringing recipients of such corrective needle maneuvers. Accordingly, physicians commonly follow and adjust the progress of the needle tip towards the interrogation region by watching the image of both displayed by the ultrasound system.

Cleanliness, it is said, is next to godliness. In the context of surgical procedures, however, not even godliness may suffice, since surgical instruments such as a guide for biopsy needles or cannulae should preferably be autoclaved to not only clean but also to sterilize the guide.

Moreover, in many known needle guides, one inserts the needle into a fixed tube, sleeve, or other channel. One disadvantage of these fixed-diameter devices is that they—by definition—cannot accommodate a wide range of needle diameters. In addition, in such guides, it may be difficult if not altogether impossible to properly clean and sterilize the inside of the tube or channel. This is often not a problem, since the guides are intended only for a single use, but this itself brings out the problem that these disposable devices are wasteful and costly. Furthermore, it is potentially dangerous for the physician to have to insert a fragile needle carefully into and through a small hole, all the while holding an ultrasonic probe. It would be preferable to have a needle guide into which the needle could be inserted safely and easily yet be guided precisely, which can be used with different needle diameters, and which can be reused yet be easily sterilized.

Another desirable feature for a needle guide is that it should have an adjustable mounting arrangement, so that the guide can be used with a variety of probes of different thicknesses.

Conventional guides for needle and cannulae include those disclosed in the following patents:
U.S. Pat. No. 5,095,910 (Powers, 17 Mar. 1992);
U.S. Pat. No. 5,076,279 (Arenson et al., 31 Dec. 1991);
U.S. Pat. No. 4,911,173 (Terwiltiger, 27 Mar. 1990);
U.S. Pat. No. 4,883,059 (Stedman et al., 28 Nov. 1989);
U.S. Pat. No. 4,742,829 (Law et al., 10 May 1988);
U.S. Pat. No. 4,681,103 (Boner et al., 21 Jul. 1987);
U.S. Pat. No. 4,635,644 (Yagata, 13 Jan. 1987);
U.S. Pat. No. 4,346,717 (Haerten, 31 Aug. 1982); and
U.S. Pat. No. 4,058,114 (Soldner, 15 Nov. 1977).

All of these known guides fail to include one or more of the desirable features discussed above.

SUMMARY OF THE INVENTION

The invention provides a guide for guiding a needle for insertion into a patient during a surgical procedure that has a main guide body, a mounting arrangement for attaching the main guide body onto an ultrasound probe, and a needle cap that fits removably onto the needle guide. At least one channel is located between the main guide body and the needle cap. During the surgical procedure, the needle is inserted into the channel. The channel, and thus the needle, is oriented at a predetermined angle relative to the ultrasound probe. The channel may be formed in either the needle cap, in the main guide body, or in both.

The needle cap is preferably made of a magnetic metal, and a magnet is preferably mounted in the main guide body. The needle cap is thus removably held on the main guide body by the force of the magnet. The magnet is preferably a rare earth magnet, and most preferably a samarium cobalt magnet, which has great magnetic strength and retains this strength even when subjected to the temperatures found in sterilizing autoclaves.

In a multi-angle embodiment of the invention, there are a plurality of channels, each having a different, predetermined guide angle.

The mounting arrangement preferably is in the form of a clamp, with a first and a second arm. The second arm is preferably pivotably secured to the main guide body, and an adjustment arrangement, for example, a thumbscrew, is provided on the second arm. The angular position of the second arm relative to the main guide body, and the distance between the first and second arms, is thereby made adjustable so that the guide can be mounted on transducer probes of different thicknesses.

BRIEF DESCRIPTION OF THE DRAWINGS

FIG. 7 is an end view of the single-angle needle cap of FIGS. 1–5.

FIG. 8 is a top view of a multi-angle needle guide, with a multi-angle cap mounted.

FIG. 9 is a top view of the multi-angle needle guide, with a multi-angle cap mounted.

DETAILED DESCRIPTION

Figure 1:
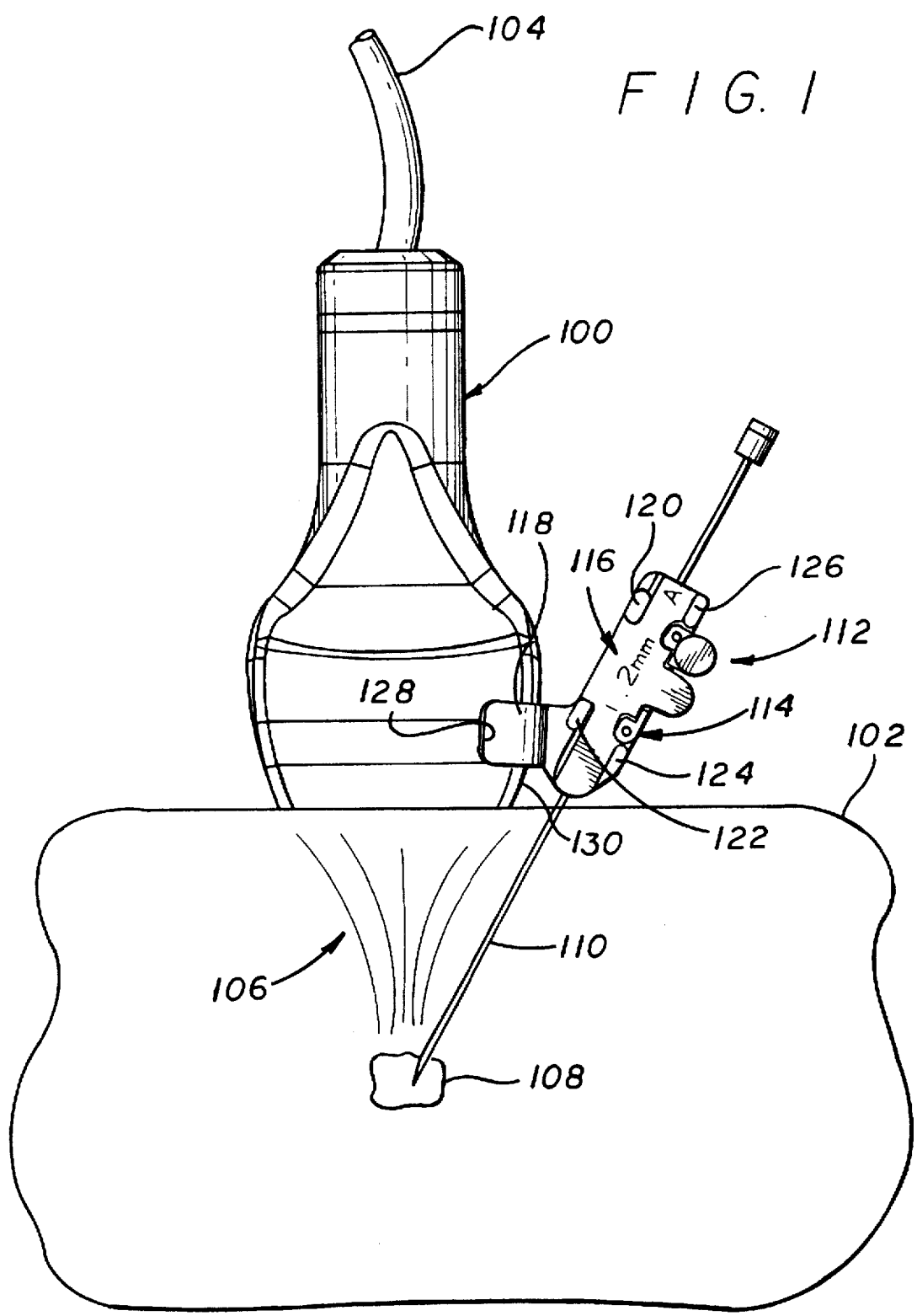
FIG. 1 is a top view of a single-angle needle guide according to the invention mounted with a biopsy needle on an ultrasound probe.

In FIG. 1, an ultrasound transducer probe 100 is shown in place against the body 102 of a patient. As in known systems, the probe is connected by a cable to various conventional driving, processing and display circuits (not shown) that generate transmission and driving signals for the piezoelectric array (also not shown) in the probe. The array thereby generates an ultrasonic beam (illustrated in FIG. 1 as scan lines 106) that is focused into an interrogation region 108, that is, a region of interest in the patient's body. The acoustic echo signals from the region 108 return to the array and are converted back into electrical signals, which are processed in any known manner to generate a visual representation of the region on a display. The general arrangement of an ultrasonic imaging system, as well as its methods of operation, are well known and are therefore not described further.

Assume now that a physician wishes to insert into the anxious patient some form of needle 110, so that the tip of the needle extends into the interrogation region 108. Examples of needles include biopsy needles, needles for drainage, amniocentesis, precision injections, or cell aspiration, or some other slender, penetrating device such as a cauterization probe. Merely by way of example, it is assumed in this description that the physician wants to insert a biopsy needle in order to get a tissue sample from the interrogation region.

In order to make the following description easier to understand, the terms "front" or "top" mean the surfaces of the probe and needle guide that are visible in FIG. 1. "Rear" and "bottom" mean the parts or surfaces opposite these.

The needle 110 is guided and secured by a needle guide, which is indicated generally as the guide 112. The main features of the guide 112 are a main guide body 114, a removable, exchangeable needle cap 116 that fits and is held onto the main body, and a mounting arrangement 118, which is attached to or is an integral portion of the main body 114.

The main body 114 also has ridge- or pin-like guide datums 120, 122, 124, 126 that accurately position the needle cap onto the main body. The needle cap 116 has indentations that correspond to the respective datums. The cap thus abuts each datum when mounted. In order to keep the assembly compact and reduce the risk that the cap will be knocked loose, however, the cap preferably does not extend beyond the edges of the main body, except for a finger tab, which is described below. Instead of datums that the cap abuts, other alignment arrangements may be used. These include mating pins and holes, or a combination of both holes and abutting indentations.

The mounting arrangement 118 preferably includes, for example, arms with protrusions (FIG. 2) that fit into respective indentations, recesses or grooves on either side of the probe 100, as well as in a side surface 130 of the probe, to fix the position of the needle guide relative to the probe. In FIG. 1, a front arm 118 is shown engaging an indentation 128 in the front face (viewed as in the figure) of the probe.

The main body 114 and parts securely attached to it are preferably machined from austenitic stainless steel, or of some other strong, stain- and corrosion-resistant, non-magnetic metal. The needle cap is preferably machined from martensitic stainless steel, or from some other strong, stain- and corrosion-resistant magnetic (that is, capable of being attracted by a magnet) metal. The preference for steel or another metal is because, unlike plastic, it not only will not wear out or fatigue as quickly as plastic, but it also allows the needle guide to be autoclaved and sterilized. The preference with respect to magnetic properties is explained further below, but, in summary, it is because the needle cap in the preferred embodiment of the invention is held on the main body magnetically, by means of a strong, preferably rare-earth (for magnetic strength and thermal stability) magnet mounted in the main body.

For any given depth in the patient's body 102 of the interrogation region 108 beneath the surface, that is, beneath the application surface of the probe 100, and for any given mounting distance between the centerline of the probe and the needle guide, there will be one angle (or narrow range of angles) at which the needle is properly guided into the interrogation region. This angle, marked "A" on the needle cap 116 in FIG. 1, will normally represent the angle made by the needle with the vertical centerline of the probe (the axial direction). The angle can be calculated easily using well-known formulas found in any standard text on elementary trigonometry. According to the invention, for different angles, different corresponding needle caps are preferably provided to align the needle at different angles; each needle cap is then marked with a corresponding, predefined marking (such as "B" or the angle in degrees, etc.) to identify the insertion angle for the physician.

As is explained in greater detail below, different needle caps are preferably provided for needles of different diameters, "gauges," or some other measure of size. This is preferably also marked on each needle cap. In FIG. 1, the needle cap is marked "1.2 mm" to indicate an example of a typical biopsy needle's diameter.

Figure 2:
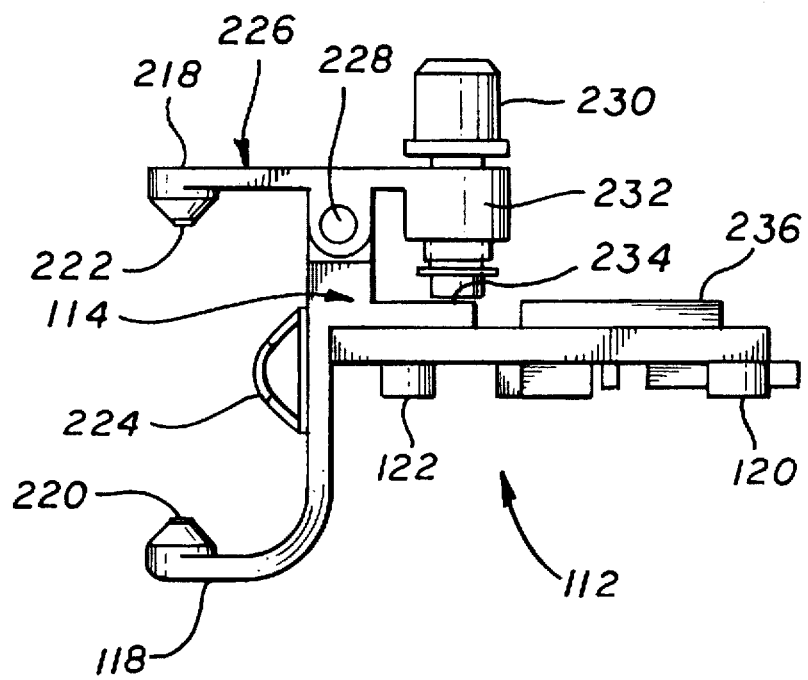
FIG. 2 is a side view of the needle guide, which also shows a preferred adjustable mounting arrangement, but with a needle cap removed.

FIG. 2 is a side view of the needle guide that better illustrates the mounting arrangement. Opposite the front mounting arm 118, which, in this example, is fixed, is a rear, pivoting mounting arm 218. The mounting arms 118, 218 have respective protrusions 220, 222 that extend mainly towards each other and fit into and mate with corresponding indentations (for the protrusion 118, the indentation 128 shown in FIG. 1) on the housing of the probe. A side protrusion 224 is formed as a portion of or is attached to the base of the fixed mounting arm. The side protrusion 224 fits into and mates with a corresponding indentation in the side the side surface 130 of the probe (see FIG. 1). When the needle guide is mounted on the probe, the protrusions 220, 222, and 224 and the mating indentations on the probe fix the guide in a known position so that the insertion angle and lateral offset of the guide will be known and secured. The protrusions 220, 222, 224 are preferably smoothly rounded to avoid any risk of scratching or puncturing of the probe surfaces on which the needle guide is attached.

The rear arm 218 is a portion of a pivoting member 226, which pivots about an axis 228 formed, for example, by a pin that is mounted in the main body 114. Opposite the rear arm 218 on the pivoting member 226 is an adjustable thumbscrew 230, which is preferably threaded and extends through a mating, threaded block portion 232 in the pivoting member. An inner end of the thumbscrew 230 abuts a contact surface 234 on the main body 114.

As the screw 230 is tightened, the pivoting member 226 pivots counterclockwise (viewed as in FIG. 2 and assuming conventional right-handed threading) so that the rear mounting arm 218 and its protrusion 222 move toward the front mounting arm 118 and its protrusion 220. The physician can thus adjust the gap between the two mounting arms 118, 218 so that the same needle guide can be mounted on probes of different thicknesses. To mount the needle guide, the physician loosens the screw 230 to open the gap, place the guide over the side edge of the probe so that the various protrusions are at least roughly aligned with their corresponding indentations, and she then tightens the screw. The diameter of the head of the screw is therefore preferably small enough that the screw will not be over-torqued and lead to damage of the normally plastic casing of the transducer probe on which the needle guide is mounted.

This preferred mounting arrangement is particularly advantageous in the common case in which the needle guide and needle are in the sterile field of the surgical procedure, but the ultrasound probe itself is not. In these cases, the ultrasound probe is typically covered by a sterile sheath, which is typically made of Latex or of some other flexible synthetic material. The needle guide is then mounted over the sheath. Using know needle guide mounts, there is a tendency to subject the sheath to rolling and shearing stresses where the guide contacts the sheath. These stresses frequently lead to puncturing of the sheath, and resulting violation of the sterile field. The mounting arrangement according to the invention allows for gentler, controlled, non-torquing and non-shearing mounting of the guide onto the probe and thus greatly reduces the risk of puncturing the sheath.

Other mounting arrangements are also possible. For example, protrusions could be provided on the probe, with corresponding recesses or holes in the mounting arms 118, 218. This would allow retrofitting of the needle guide onto existing probes, for example by gluing, ultrasonic welding, or heat-staking protrusions onto the probe housing. A disadvantage, however, is that the probe housing could then no longer be made substantially smooth; this in turn might reduce user comfort somewhat and the protrusions then might also be worn down with use or knocked off.

It is also possible to forego the threaded screw in favor of a pin that is spring-biased, with its inner end pressing against the surface 234, so that the spring will tend to close the gap between the mounting arms. Although this system avoids the need for the physician to adjust a screw, the preferred screw adjustment provides a more secure grip on the probe, with no concern for weakening spring force over time, and will typically be easier to clean and sterilize than most springs.

FIG. 2 also shows a magnet bracket or holding strap 236, which is attached securely in any known heat-resistant manner to the rear of the main body of the needle guide. The purpose of this strap is to support a cap-retaining magnet, the purpose and nature of which are explained further below.

Figure 3:
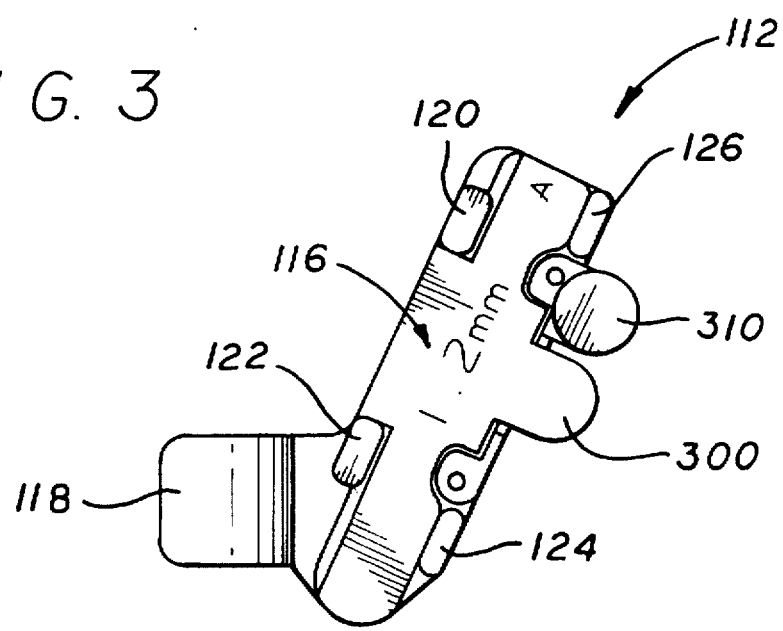
FIG. 3 is a top view of the needle guide alone, including a single-angle needle cap.

FIG. 3 shows the needle guide according to the invention, with the needle cap 116 in place. In order to make it easier to remove the needle cap from the main body, the cap and main body preferably have non-overlapping but opposing finger tabs 300, 310. The finger tab 300 is preferably simply a protruding position of the cap itself, whereas the tab 310 may either be an integral portion of the main body or may be attached to it as a separately machined member. To quickly remove the needle cap 116, the user may, for example, press down on the tab 310 with the thumb of his right hand and simultaneously lift up on the tab 300 with either the tip of his right middle finger or the side of his index finger.

Figure 4:
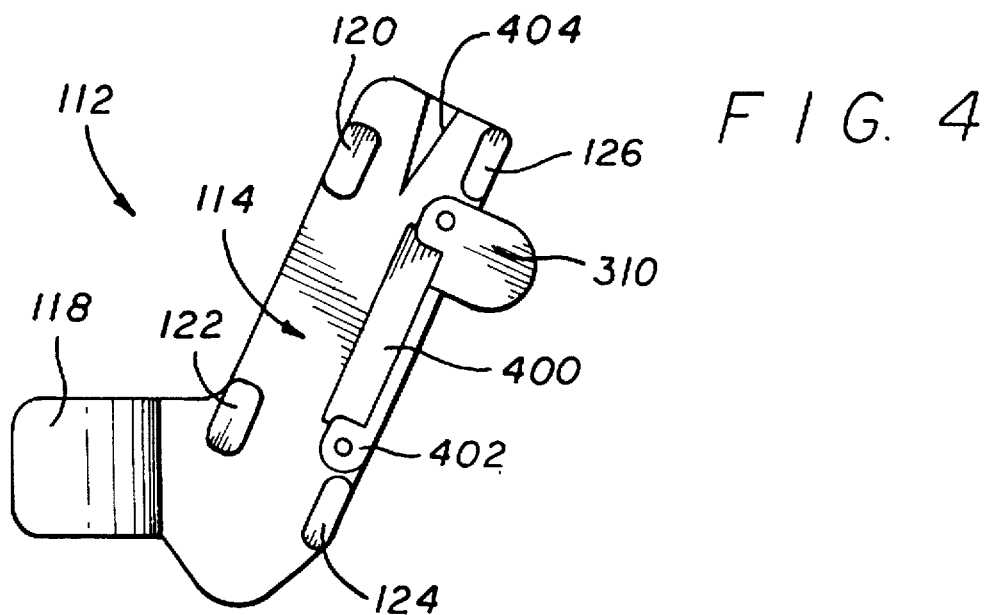
FIG. 4 is a top view of the needle guide of FIG. 3 with the needle cap removed.

FIG. 4 illustrates the top side of the needle guide 112 with the needle cap removed. According to the preferred embodiment of the invention, a magnet 400 is mounted in the main body 114 of the needle guide, preferably flush with the upper surface of the main body. The magnet may be glued into place or otherwise installed permanently. In the preferred embodiment, however, the magnet it is held in place by edge holders, which may be separate members such as holder 402, or may be a portion of some other attached member such as the inner end of the thumb tab 310. The edge holders are preferably secured to the main body using press-fitted (also known also "interference fitted") pins; they may, however, also be attached using screws. This arrangement with press-fitted pins or screws allows the magnet to be replaced. Note that the holder 402 or tab 310, or both, can be used in place of (rather than just in addition to) one or both of the guide datums 124, 126, although it is preferred to include the datums 124, 126 since they are more widely separated (thus reducing any possible play of the cap) and are not subject to misalignment once installed.

Recall that the main body 114 and parts securely attached to it are preferably machined from austenitic stainless steel, or of some other non-magnetic metal, whereas the needle cap is preferably machined from martensitic stainless steel, or from some other magnetic metal. When the needle cap is laid between the guide datums 120, 122, 124, 126, the force of the magnet will hold it in place. The use of a magnet to hold the needle in place has several advantages over known devices. First, the needle cap can be mounted and changed quickly. Second, the mounting arrangement is simple, with no screws, and easy to keep clean. Third, the arrangement is long-lasting and not subject to material fatigue, as can be the case with snap-on plastic caps or caps that rely on some friction mounting.

It is, however, important that the needle cap, and thus the needle, should be held securely. In general, the magnet 400 may be of any known ferrous or non-ferrous type. In the preferred embodiment of the invention, the magnet 400 is a rare earth magnet, since such magnets are magnetically much stronger for a given size than ferrous magnets and they have a higher resistance to demagnetization. Suitable rare earth magnets include samarium cobalt magnets (SmCo, sometimes with some iron) and neodymium magnets (Nd—Fe—B, usually with some transition metals). A samarium cobalt magnet is preferred in the invention because it retains its magnetic strength up to a temperature of about +300° C. and will therefore not lose its magnetization in an autoclave. By comparison, a neodymium magnet has a maximum operating, demagnetization temperature of roughly +80° C. Since the needle guide can thus be made entirely of heat-resistant metals and materials, it can be autoclaved and sterilized repeatedly, with no need to dispose of any part of the guide.

It is also possible for the main body to be made of a magnetic metal. Because of the strength of the preferred rare earth magnet, however, this may make it difficult to remove the needle cap from the main body. Prototypes of the invention have shown that more than sufficient holding force for the cap can be achieved with a non-magnetic main body.

As FIG. 4 illustrates, a tapering, wedge-shaped recess is preferably cut into the top of the main body so that, at its lower tip, it is flush with the surface of the main body. Together with a groove (see below) in the needle cap, this recess helps form an opening wider than the groove itself so as to make it easier for the user to insert the tip of the needle into the guide when the needle cap is in place.

Figure 5:
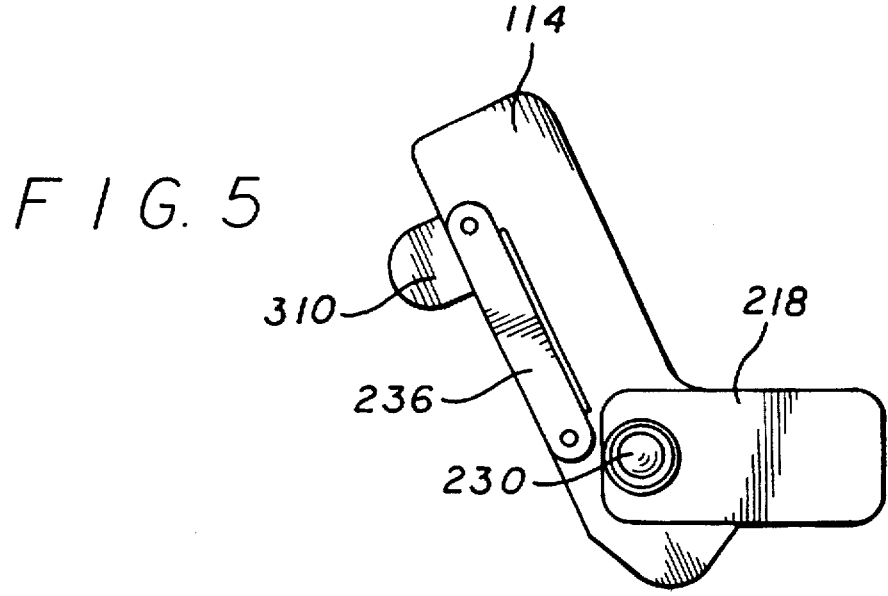
FIG. 5 is a rear view of the needle guide of FIG. 4.

FIG. 5 shows the rear of the needle guide, that is, the reverse view relative to FIG. 4. In FIG. 5, the holding strap 236 for the magnet is also shown. One advantage of the holding strap is that it allows the main body of the needle guide to be narrow, thus reducing weight and cost. If the portion of the main body where the magnet is mounted is thick enough, the magnet could instead be mounted in a recess in this portion, with no need for the strap 236.

Figure 6:
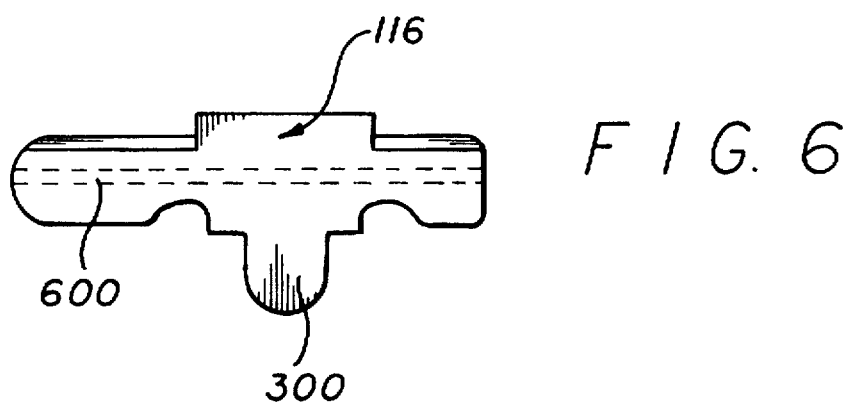
FIG. 6 is a bottom view of the single-angle needle cap of FIGS. 1–4.

FIG. 6 shows the single-angle needle cap 116. A groove 600 runs the length of the cap and forms a channel into and through which the needle is inserted when the needle guide is in use.

FIG. 7 is an end view of the single-angle needle cap 116 according to the invention. In the preferred embodiment, the groove 600 has a cross-section like a truncated equilateral triangle whose depth is chosen using normal formulas to provide three-point contact for the needle 110. In other words, the cross-section of the needle 110, when in the groove, touches the wall of the groove at two points and is flush with (or just very slightly below) the upper surface 700 of the cap so that it will also just touch (or preferably, to reduce friction, fall just short of touching) the upper surface of the main body 114 (see FIG. 4). This provides secure, well-spaced, three-point contact for holding the needle. For any given needle diameter, the dimensions of the groove will be determined.

The groove need not have the preferred cross-sectional shape. Instead, it could have any "V" shape; it could be semi-circular, rectangular, or any other shape that allows the needle to move between the needle cap and the main body of the needle guide, although one must keep in mind the twin goals of securely guiding the needle and minimizing friction.

Refer to both FIG. 4 and FIG. 6. It is also possible to form at least a part of the groove 600 in the surface of the main body 114. The disadvantage of this choice, however, is that the needle guide cannot then be optimized for different needle diameters.

FIGS. 8 and 9 illustrate an embodiment of the invention with which a needle may be guided at more than one angle. Parts and portions of this embodiment that are the same as or closely analogous to those described for the single-angle embodiment retain the same reference numbers. In the illustrated embodiment, there are three grooves 900A, 900B, 900C corresponding to predefined needle angles A, B and C, respectively. By way of example only, the grooves are formed in the surface of the main body 114. Multiple grooves may, of course, instead be formed in the underneath side of the needle cap 916, with the main body having a smooth surface, except perhaps for an introduction opening such as the recess 404 shown in FIG. 4. Although not necessary, the grooves preferably "fan out" upward from a single lowermost groove portion 918, since this allows the lower portion of the cap to be kept as narrow as possible.

The number of grooves need not be limited to three, but rather can be any number within the realm of normal engineering practicality and of the needs of the procedures in which the needle guide is going to be used. The number of angles (grooves) in the multi-angle embodiment of the invention will depend, for example, on how large a needle guide one is willing to accept, the needs, including the required geometry, of the procedures one expects to perform with the needle guide, and the gauge of needles to be used.

Note that it is not necessary according to the invention for all of the grooves to have the same cross-sectional area or shape. It is also possible to include grooves that do not intersect at all, or that intersect at a place beside their lowermost ends. Multiple grooves may even be parallel, so that the needle angle relative to the probe will stay the same but the penetration depths will be different. Needles of different diameters could then also be used in a single needle guide.

We claim:

1. A device for guiding a needle for insertion into a patient during a surgical procedure, comprising:

a re-usable and heat-sterilizable main guide body;

a mounting arrangement for attaching the main guide body onto an ultrasound probe, the mounting arrangement being adapted to engage the ultrasound probe and to maintain an angular arrangement between the ultrasound probe and the main guide body;

a needle cap made of a magnetically attracted material;

a channel that is located between the main guide body and the needle cap, that is oriented at a predetermined angle relative to the ultrasound probe, and in which the needle is circumferentially enclosed and is slidably positioned during the surgical procedure; and a magnet mounted in the main guide body securely but removably holding the needle cap on the main guide body, thereby also securely but slidably holding the needle in the channel.

2. A device as in claim 1, in which the main body is non-magnetic and the magnet is a rare earth magnet.

3. A device as in claim 1, in which:

the mounting arrangement has a first and a second arm;

the second arm is pivotably secured to the main guide body;

an adjustment arrangement is provided on the second arm, the angular position of the second arm relative to the main guide body, and the distance between the first and second arms, thereby being adjustable; and the first and second arms form a clamp that securely but removably engages the ultrasound probe.

4. A device for guiding a needle for insertion into a patient during a surgical procedure comprising:

a re-usable and heat-sterilizable main guide body;

a mounting arrangement for attaching the main guide body onto an ultrasound probe, the mounting arrangement being adapted to engage the ultrasound probe and to maintain an angular arrangement between the ultrasound probe and the main guide body;

a needle cap;

a channel that is located between the main guide body and the needle cap when the needle cap is mounted on the main guide body, that is oriented at a predetermined angle relative to the ultrasound probe, and in which the needle is slidably positioned during the surgical procedure; and in which:

the mounting arrangement has a first and a second arm;

the second arm is pivotably secured to the main guide body;

an adjustment arrangement is provided on the second arm, the angular position of the second arm relative to the main guide body, and the distance between the first and second arms, thereby being adjustable; and the first and second arms form a substantially U-shaped clamp that securely and removably engages but extends only partially around the ultrasound probe, the mounting arrangement thereby being adapted to securely engage ultrasound probes of different thicknesses.

* * * * *